`United States Patent` [19]

Laguerre

[11] 4,046,591

[45] Sept. 6, 1977

[54] METHOD FOR CLEANING THE EPIDERMIS USING A MAGNETIC FIELD

[76] Inventor: René Laguerre, 20 Allee du Mail, Meudon la Foret, France, 92360

[21] Appl. No.: 569,652

[22] Filed: Apr. 21, 1975

[30] Foreign Application Priority Data

Apr. 23, 1974 France ............................. 74.14086
Apr. 9, 1975 France ............................. 75.11101

[51] Int. Cl.$^2$ ............................................. B08B 7/00
[52] U.S. Cl. ........................................... 134/1; 134/7; 134/42; 424/69; 424/147
[58] Field of Search ................ 134/1, 7, 42; 424/69, 424/61, 131, 147; 128/1.3

[56] References Cited

U.S. PATENT DOCUMENTS

| | | | |
|---|---|---|---|
| 2,765,257 | 10/1956 | Blackburn | 424/61 |
| 3,487,916 | 1/1970 | Muroni et al. | 424/69 |
| 3,514,328 | 5/1970 | Malin | 134/1 |
| 3,695,934 | 10/1972 | Feldhaus | 134/1 |
| 3,708,435 | 1/1973 | Starkman | 424/69 |

*Primary Examiner*—S. Leon Bashore
*Assistant Examiner*—M. Steven Alvo
*Attorney, Agent, or Firm*—Jay L. Chaskin

[57] ABSTRACT

A method, a product and an apparatus for cleaning the epidermis, wherein a magnetic or magnetizable substance applied onto the epidermis is caused to penetrate into the pores of the skin, and is then extracted with the pollutants from the excretory ducts of the pores by being subjected to the influence of a magnet applied onto the epidermis.

The magnetic or magnetizable substance penetrates the pores of the skin by massaging the substance to insert it between the dead cells of the skin and the waste products excreted by the skin.

11 Claims, 8 Drawing Figures

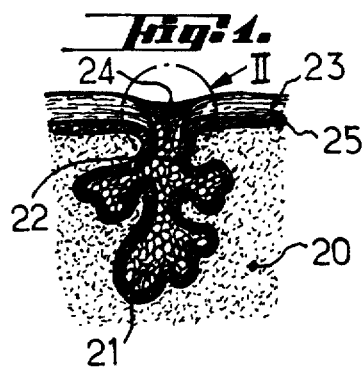
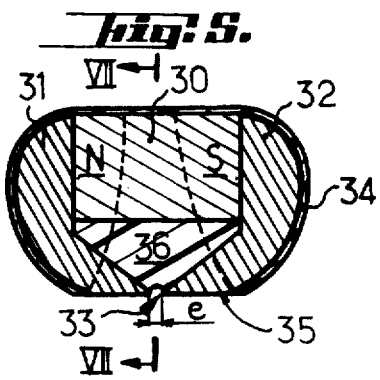
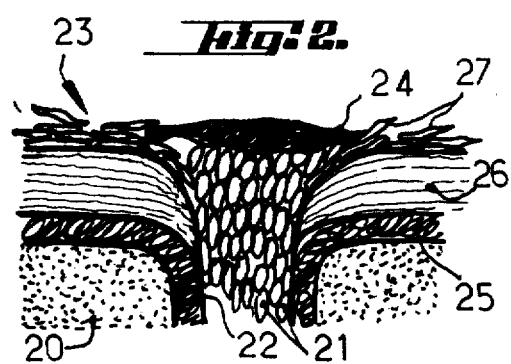
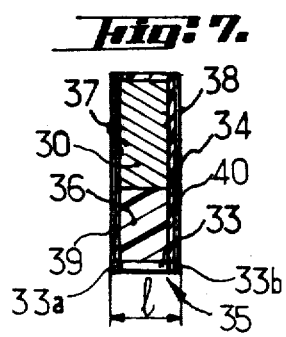
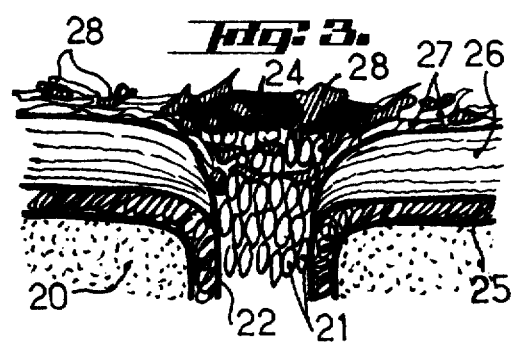
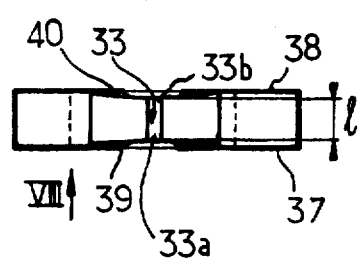
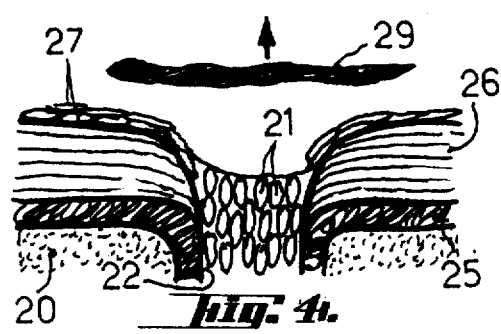
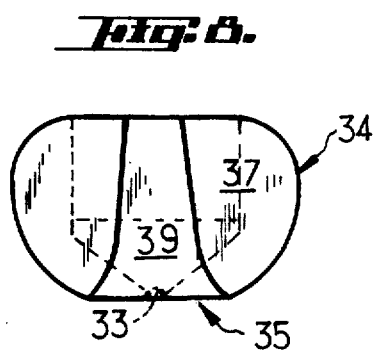

METHOD FOR CLEANING THE EPIDERMIS USING A MAGNETIC FIELD

The present invention relates to a method enabling a cleaning in depth and at the surface of the cuticle or epidermis.

It is known that the pores of the skin are tiny holes which communicate through excretory ducts with cutaneous (sweat or sebaceous) glands and that they are very often obstructed partially or totally by polluting materials.

The obstruction of the excretory ducts prevents the cutaneous glands from performing their functions properly. Thus the sebaceous glands do no longer secrete the sebum required for the lubrication of the epidermis or cuticle and the function of which is to prevent the skin from drying up, the sweat or sudoriferous glands do not longer secrete the sweat the acidity of which prevents the developments of the micro-organisms, the free operation of these latter glands being in addition required for removing toxins generated by the body.

The method according to the invention enables to overcome these inconveniences by a natural cleaning of the cuticle or epidermis in depth and at the surface, i.e. without any aggression or attack of chemical, physical, physiological or other nature.

For this purpose the method according to the invention is characterized in that it consists in:

causing a magnetic or magnetizable substance applied onto the cuticle or epidermis to penetrate into the pores of the skin, extracting the polluting materials or pollutants from the excretory ducts of the pores by subjecting said substance to the influence of an extraction means applied onto the epidermis or cuticle.

According to this interesting characterizing feature the pollutants and mainly the seborrheal accummulations or amounts in excess which obstruct the pores are converted into magnetic substances easily extracted by the means placed close to or in contact with the skin.

According to another characterizing feature of the invention said substance is formed by incorporating a magnetic or magnetizable material into an excipient or vehicle.

If the magnetic substance comprises a magnetizable material the process consists in generating an outside magnetic field by a magnetized part or member for extracting the pollutant admixed to the magnetic substance. If the magnetic substance comprises a previously magnetized material it is possible to use either an outer magnetizable circuit which closes the lines of force between the different polarities of said material or a magnetic field as in the first case. In any case the magnetized part or member or the magnetizable circuit is adapted to the conformation of the cuticle or epidermis and also to the convenience or easiness of gripping or grasping by the user.

It has been found that the sufficiently fine magnetic or magnetizable particles of which the substance used is consisting would indeed insert or move themselves between the dead superficial cells of the skin and into the sweat and sebaceous ducts and could then be extracted by means of the magnet while carrying along therewith a part of the external dead cells of the skin as well as the waste products, the polluting foreign or extraneous particles and the excess sebum essentially contained at the outlets or issues of the sweat and sebaceous ducts.

Tests have shown that the best results were obtained when according to the invention use was made of powders consisting essentially of particles exhibiting a grain size small enough for enabling to cause the powder to be introduced through simple massage between the dead superficial cells of the skin and into the sweat and sebaceous ducts.

According to a further characterizing feature of the invention the shapes of said particles is selected so that they are substantially ovoid and exhibit rugosities thereby providing for a better action for performing the desired or sought cleaning of the skin in depth.

The invention moreover covers a product enabling to apply the process according to the invention.

The product is characterized in that it includes a magnetic or magnetizable substance comprising magnetic or magnetizable particles incorporated into an excipient which serves as an applicator vehicle.

The magnetic or magnetizable particles are impalpable and consist for instance of iron-nickel. The excipient is either a dermo product (such as for instance : creams, milk, pastes, gels and compounds) or a physiological serum.

According to the invention said product is also characterized in that the magnetic or magnetizable powder used has preferably a grain size smaller than about 80 microns.

The invention is also directed to an apparatus enabling to carry out the method, said apparatus being characterized in that it comprises a magnet and polar masses or bodies which confine and guide the magnet flux into an air-gap ranging from one to a few millimeters said air-gap consisting of one face or side of the apparatus shaped so as to be easily passed or moved over the skin in particular along the outlines of the face.

The invention will be better understood and further objects, characterizing features, details and advantages thereof will appear more clearly as the following explanatory description proceeds with reference to the accompanying diagrammatic drawings given by way of non-limitative examples only illustrating presently preferred forms of embodiments of or means for carrying out the invention and wherein:

FIG. 1 is a view drawn on a large scale in cross-section showing a sebaceous gland with its duct opening at the surface of the cuticle or epidermis;

FIG. 2 is a view drawn on a larger scale of the encircled detail portion II in FIG. 1;

FIG. 3 is a view similar to that of the FIG. 2 showing in this area the penetration of the particles used according to the invention in a first stage or operating step for cleaning the skin;

FIG. 4 shows how the skin presents itself at the section in FIG. 3 after extraction of the particles previously inserted and simultaneous carrying along of the dead cells and pollutants at the outlet of the sebaceous duct;

FIG. 5 shows in section a device enabling the convenient extraction of the magnetic particles;

FIG. 6 is a bottom view of the device shown in FIG. 5;

FIG. 7 is a view of cross-section taken substantially upon the transverse center-plane VII—VII in FIG. 5; and FIG. 8 is a side view of the device as viewed in the direction of the arrow VIII in FIG. 6.

Reference should at first be had to FIG. 1 in which is diagrammatically seen as drawn on a larger scale a sebaceous gland 20 which emits or secretes sebum 21 which is excreted through the duct 22 so as to be caused to lubricate the outer layer 23 of the cuticle or epidermis consisting of the dead cells of the skin. At 24 is diagrammatically shown a comedo or "black head" constituted by dried up sebum admixed to pollutants such as atmospheric dust, etc. Under the outer layer 23 of the cuticle or epidermis has been also shown at 25 the basal layer which will reconstruct or restore the cuticle or epidermis.

In FIG. 2 is seen on a larger scale the skin at the outlet of the sebaceous duct 22. On that scale is better seen above the basal layer 25 of the epidermis or cuticle a layer 26 of live cells well connected to each other and an outer layer of dead cells 27 which are beginning to separate or exfoliate or scale off and which form the visible outer layer 23 of the skin. The cells 27 present themselves somewhat like tiles of roof by partially overlapping and straddling each other.

According to the invention and as shown in FIG. 3 the method consists in applying onto the skin a power consisting essentially of particles 28 which exhibit a grain size small enough to enable them to be caused to penetrate through simple massage between the dead superficial cells 27 of the skin and into the sweat and sebaceous ducts such as the duct 22.

As diagrammatically illustrated in FIG. 3 the particles 28 are selected so they have a substantially ovoid shape, i.e. a certain thickness with respect to their length and that they exhibt rugosities. Thus is avoided the possibility of injuring or hurting the skin since the particles are unable to puncture tissues but may only insert themselves or be brought into the open spaces of the skin that is between the dead cells 27 or into the sebaceous or sweat ducts.

Tests have shown that the best results were obtained with magnetic or magnetizable powders having a grain size smaller than about 80 microns. Finer particles such as those with grain sizes ranging between 10 and 40 microns are particularly effective. In practice a spectrum of grain sizes ranging from about 10 to about 80 microns should be used although finer powders could be used. When the particles exceed a grain size of 80 microns an unpleasant physiological feeling or sensation is usually felt.

The particles 28 possibly admixed to or blended with an excipient (a cream, a milk, a paste, a gel) which excipient does not penetrate into the skin and has not been shown for sake of clarity are thereby introduced into the outer surface of the cuticle or epidermis below the dead cells 27 of the skin as well as into the sweat and sebaceous ducts while penetrating in the latter case into the sebum and black heads more or less deeply according to the more or less great duration and intensity or strength of the massage.

Then as shown in FIG. 4 when a magnetic pull means such as a magnet is passed over the surface of the skin all the magnetic or magnetizable particles 28 are collected or gathered and they carry along therewith in the form of a heap 29 the outer dead cells 27 of the skin, the black heads 24 and the excess amounts of sebum at the outlets of the sebaceous ducts 22.

In order to make effective the extraction of the magnetic particles 28 and pollutants they carry along an apparatus such as described hereinafter with reference to FIG. 5 to 8 may be used advantageously.

According to the form of embodiment shown in these figures, the apparatus consists essentially of a magnet 30 the poles N, S of which are lying between two polar bodies or faces 31, 32 made for instance from soft iron and which are confining and guiding the magnetic flux into an air-gap 33 which may advantageously have the shape of a substantially straight through with a width $e$ equal to one or two millimeters and a length $l$ of about one to a few millimeters. The magnet 30 and the polar bodies or faces 31, 32 are advantageously lined with a covering 34 made from plastics material which is coating or wrapping the apparatus while leaving bare the lower face or bottom side 35 which will be passed over the skin. Moreover in order to avoid the introduction of foreign or extraneous matters into the apparatus the space 36 left between the magnet 30 and the polar bodies or faces 31, 32 should advantageously be filled with a plastics material such as araldite.

In order to facilitate the cleaning of the device after use there should advantageously be provided on those outside faces 37, 38 of the apparatus which are substantially normal to the air-gap line 33 and lie substantially in the center-plane of the apparatus two grooves 39, 40 or flutes which lead to or terminate in the side ends 33a, 33b of the air-gap.

With such conditions the manner of using the invention is the following:

One applies onto the face while effecting a slight massage the magnetic or magnetizable powder which will usually be included in a vehicle such as a cream, a milk, a paste, a gel and the function of which is to avoid spreading or spilling the powder about oneself. Then the excess amount of cream and powder should be removed by means of a towel so as to avoid clogging or fouling the apparatus which will effect the extraction of the powder having penetrated into the skin. Then the extractor apparatus such as the one depicted in FIGS. 5 to 8 will be passed on the surface of the face. In the air-gap 33 will be collected the particles extracted from the skin admixed to the dead cells and the different pollutants which have been extracted at the same time. There remains only to clean the apparatus by slidingly pushing the particles pushed into the air-gap 33 for instance by means of a cotton wool by bringing or moving them to one of the ends 33a, 33b of the air-gap into one of the grooves 39 or 40 where they may easily be extracted because the magnetic field quickly becomes substantially zero in this region of the apparatus.

Many improvements to the form of embodiment described may be made.

Thus for instance the extractor apparatus may be shaped as desired for properly conforming to the skin surface for instance like a shaver head. An electromagnetic system or appliance may also be substituted for the permanent magnet although the latter is preferred in most of the cases taking into account its light weight and good effectiveness.

It is also possible to admix to or blend with the magnetic or magnetizable power a non-magnetic or non-magnetizable powder for instance of quartz or of a volcanic rock, such as pumice-stone, which is biologically inert. The range of the grain size of the inert powder is; preferably selected to be at last equal to or larger than that of the magnetic powder and which without clearly penetrating into the skin will promote the penetration of the magnetic powder for example, the inert powder may have a grain size range from 40 to 80 microns and the magnetic or magnetizable powder is less than 40 micrometers.

The invention thus comprises all the technical equivalents of the means described as well as their combinations if the latter are carried out according to its gist and used within the scope of the appended claims.

What is claimed is:

1. A method of cleaning the epidermis of the skin comprising the steps of
   applying onto the epidermis a particulate substance comprising particles having a grain size between 10 and 80 microns and which can be displaced by the action of a magnetic field, the particles having a shape for penetrating the pores and hollows of the skin without injuring the skin;
   causing by massaging said particulate substance to penetrate the pores and hollows of the skin and to insert between the dead cells of the skin and the waste products excreated by the skin;
   applying and moving on the surface of the epidermis a magnetic field having its action concentrated on a width and length not exceeding a few millimeters, and retracting said particulate substance by action of said magnetic field, carrying therewith a part of said dead cells and waste products from the skin.

2. A method according to claim 1, comprising the step of providing said substance by incorporating the particulate material into a vehicle.

3. A method according to claim 2, wherein said vehicle is a cosmetic product.

4. A method according to claim 2, wherein said vehicle is physiological serum.

5. A method according to claim 1 wherein said particulate substance is a powder for penetration between the dead superficial cells of the skin and into the sweat and sebaceous ducts.

6. A method according to claim 5, wherein the grain size is between 10 and 40 microno.

7. A method according to claim 5, wherein said particles are selected so that they have a substantially ovoid shape and are formed with rugosities.

8. A method according to claim 5, wherein to said powder is added an inert powder which cannot be displaced by the action of a magnetic field.

9. A method according to claim 8, wherein the inert powder has a grain size range at least equal to the magnetically responsive powder.

10. A method according to claim 8, wherein the inert powder has a grain size range larger than that of the magnetically responsive powder.

11. A method according to claim 8, wherein the inert powder has a grain size range from 40 to 80 microns and the magnetically responsive powder has a grain size less than 40 microns.

* * * * *